United States Patent [19]

Szinyei

[11] Patent Number: 5,241,868
[45] Date of Patent: Sep. 7, 1993

[54] SAMPLE DISPERSING APPARATUS AND METHOD FOR USE WITH A PYROLISIS FURNACE

[75] Inventor: W. Jay Szinyei, Houston, Tex.

[73] Assignee: Baker Hughes Incorporated, Houston, Tex.

[21] Appl. No.: 828,019

[22] Filed: Jan. 30, 1992

[51] Int. Cl.⁵ .................. G01N 31/12; G01N 21/72
[52] U.S. Cl. ................. 73/863.71; 73/23.20; 73/23.42; 422/94; 436/154
[58] Field of Search ............... 436/127, 154; 210/692; 422/94; 73/23.2, 863.71, 23.42

[56] References Cited

U.S. PATENT DOCUMENTS

| | | | |
|---|---|---|---|
| 3,103,807 | 9/1963 | Broerman | 73/23.42 |
| 3,612,039 | 10/1971 | Falk | 73/23.2 |
| 3,661,527 | 5/1972 | Eggertsen et al. | 436/154 |
| 3,753,654 | 8/1973 | Eggertsen | 436/154 |
| 4,601,882 | 7/1986 | Benner | 422/80 |
| 4,684,251 | 8/1987 | Brouwer et al. | 356/315 |
| 4,688,436 | 8/1987 | Richon et al. | 73/863.71 |
| 4,798,805 | 1/1989 | Issenmann | 436/154 |
| 4,904,606 | 2/1990 | Forster et al. | 261/76 |
| 4,919,892 | 4/1990 | Plumb | 73/863.71 |
| 5,019,517 | 5/1991 | Coulson | 73/23.2 |
| 5,088,315 | 2/1992 | Johnson | 73/23.2 |

*Primary Examiner*—Hezron E. Williams
*Assistant Examiner*—George M. Dombroske
*Attorney, Agent, or Firm*—Sroufe, Samecki, Payne & Lundeen

[57] ABSTRACT

An apparatus for dispersing a sample for use in combination with a pyrolysis furnace for measuring the concentration of a fluid in a process stream or environment is provided. A conduit is provided having a first end for receiving the sample and a second end through which the sample exits. The pyrolysis furnace surrounds the second end of the conduit for heating the conduit and any sample passing there through. A dispersing device is used to distribute the sample throughout the conduit such that the sample is heated in the conduit by the pyrolysis furnace without causing coking within the conduit. Also, a method for dispersing a sample for use in combination with a pyrolysis furnace for measuring the concentration of a fluid in a process stream or environment is provided. The method comprises the steps of receiving a sample into a first end of a conduit having a channel there through, passing the sample down the channel in the conduit, dispersing the sample throughout the cross section of said conduit, moving the dispersed sample down the channel in the conduit, and engaging the dispersed sample in the channel of the conduit with the pyrolysis furnace for initiating the pyrolization. Preferably, the dispersing device is quartz wool.

7 Claims, 1 Drawing Sheet

SAMPLE DISPERSING APPARATUS AND METHOD FOR USE WITH A PYROLISIS FURNACE

FIELD OF THE INVENTION

The field of the invention relates generally to an apparatus and method for detecting the concentration of a fluid. Specifically, the present invention relates to an apparatus and method for dispersing a sample containing sulphur, nitrogen and other fluid compounds prior to engaging the sample with a pyrolysis furnace.

BACKGROUND OF THE INVENTION

Chemical plants, oil refineries and other industrial facilities produce fluids which present health and safety problems. In some situations, even small amounts of the fluid, for example, a few parts per million or even a few parts per billion, can constitute serious health, safety and environmental problems. Also, such fluids and gases can be a danger to workmen in the vicinity of the facility. The difficulties in detecting and determining the presence of a selected fluid in a process stream or in the environment is exceedingly difficult due to the extensive nature and the large size of industrial plants.

Thus, the detection and monitoring of fluids associated with industrial plants is highly advantageous with respect to health, safety and environmental concerns. Further, the detection and monitoring of industrial fluids can prevent other dangers such as ignition, plant failure and the like.

Further, the need to detect particular constituents in a process stream can be based on product quality, process control, regulatory requirements and financial considerations. Particular fluid constituents of interest are, for example, hydrogen sulfide and nitrogen oxides. Industrial monitoring equipment exists for all phases of industry. Particularly, a variety of equipment is available using colorimetric methods. Colorimetric monitoring is utilized in process streams and associated atmospheres in and about industrial facilities. The colorimetric equipment and methods that are prevalent include absolute darkness techniques, tape difference techniques and analog first derivative techniques. Typically using colorimetric equipment, an ambient atmosphere is passed through the apparatus whereby the fluids in question react with a color-altering material. The magnitude of the color change is proportional to the concentration of the fluid in the atmosphere.

All colorimetric methods have problems. For example, samples not dispersed cause coking on the side of the conduit when passing through a pyrolysis furnace. Also, absolute darkness techniques are subject to noise from zero fluctuation. The noise from zero fluctuations is due to the non-uniform reflectance characteristics of the colorimetric sensing media. Similarly, tape difference techniques require a zero reading. After the zero reading, a period of time must elapse between the initial reading and the final reading. The relatively long time period between readings does not take into account the nonlinearity of the sensing media and effects the response time of tape difference techniques. Analog first derivative techniques are subject to power line interferences. Further, analog first derivative techniques are limited by the current leakage in the differentiating capacitor which is typically used. Still further, the analog first derivative techniques operate in the linear portion of the response of the sensing device and require a linear response curve relationship for accurate results.

Many colorimetric analyzers generally have light sources, optics and detectors fixed in a rigid framework with light paths of the optics traversing through the ambient air. Such colorimetric analyzers require that correct alignment of the optical components be maintained during the operation of the equipment. The alignment of the optics is typically subject to environmental factors as well as mechanical problems. Examples of environmental and mechanical problems include changes in temperature, operation of equipment in high vibration environments, mechanical stress associated with typical equipment use, and the like.

Of additional concern is the environment in which the apparatus must operate. It is not unusual that the apparatus is required to be explosion proof for operation in industrial facilities. Typically, an explosion proof apparatus must be housed in a purged cabinet or housed in an explosion proof enclosure. The use of explosion proof equipment creates many problems with respect to adjustment, maintenance and calibration of the apparatus without compromising the protective environment of the explosion proof equipment.

It is, therefore, a feature of the present invention to provide a sample dispersing apparatus and method for use in combination with a pyrolysis furnace for diffusing the specimen prior to introducing the specimen into the pyrolysis furnace.

A feature of the present invention is to provide a sample dispersing apparatus and method for use in combination with a pyrolysis furnace whose scattering parameters can be changed or modified depending on the requirements of the particular analysis.

Another feature of the present invention is to provide a sample dispersing apparatus and method for use in combination with a pyrolysis furnace that provides enhanced sensitivity.

Still another feature of the present invention is utilizing a ceramic means for dispersing a sample immediately prior to entering a pyrolysis furnace.

Additional features and advantages of the invention will be set forth in part in the description which follows, and in part will become apparent from the description, or may be learned by practice of the invention. The features and advantages of the invention may be realized by means of the combinations and steps particularly pointed out in the appended claims.

SUMMARY OF THE INVENTION

To achieve the foregoing objects, features and advantages, and in accordance with the purpose of the invention as embodied and broadly described herein, an apparatus and method for dispersing a sample for use in combination with a pyrolysis furnace for measuring the concentration of a fluid in a process stream or environment is disclosed.

The apparatus for dispersing a sample for use in combination with a pyrolysis furnace for measuring the concentration of a fluid in a process stream or environment comprises a conduit having a first end for receiving the sample and a second end through which the sample passes from the conduit. The pyrolysis furnace is associated with the second end of the conduit for heating the conduit and any sample passing through the conduit. A dispersing device distributes the sample throughout the conduit such that the sample is heated in the conduit by the pyrolysis furnace without causing coking within the conduit.

The method for dispersing a sample for use in combination with a pyrolysis furnace for measuring the concentration of a fluid in a process stream or environment comprises the steps of (a) receiving a sample into a first end of a conduit having a channel there through, (b) passing the sample down the channel in the conduit, (c) dispersing the sample throughout the cross section of said conduit, (d) moving the dispersed sample down the channel in the conduit, and (e) engaging the dispersed sample in the channel of the conduit with the pyrolysis furnace for initiating the pyrolization.

Preferably, the dispersing device is quartz wool.

BRIEF DESCRIPTION OF THE DRAWINGS

The accompanying drawings which are incorporated in and constitute a part of the specification, illustrate the preferred embodiments of the invention and together with the general description of the invention given above and the detailed description of the preferred embodiment given below, serve to explain the principles of the invention.

Figure 1:
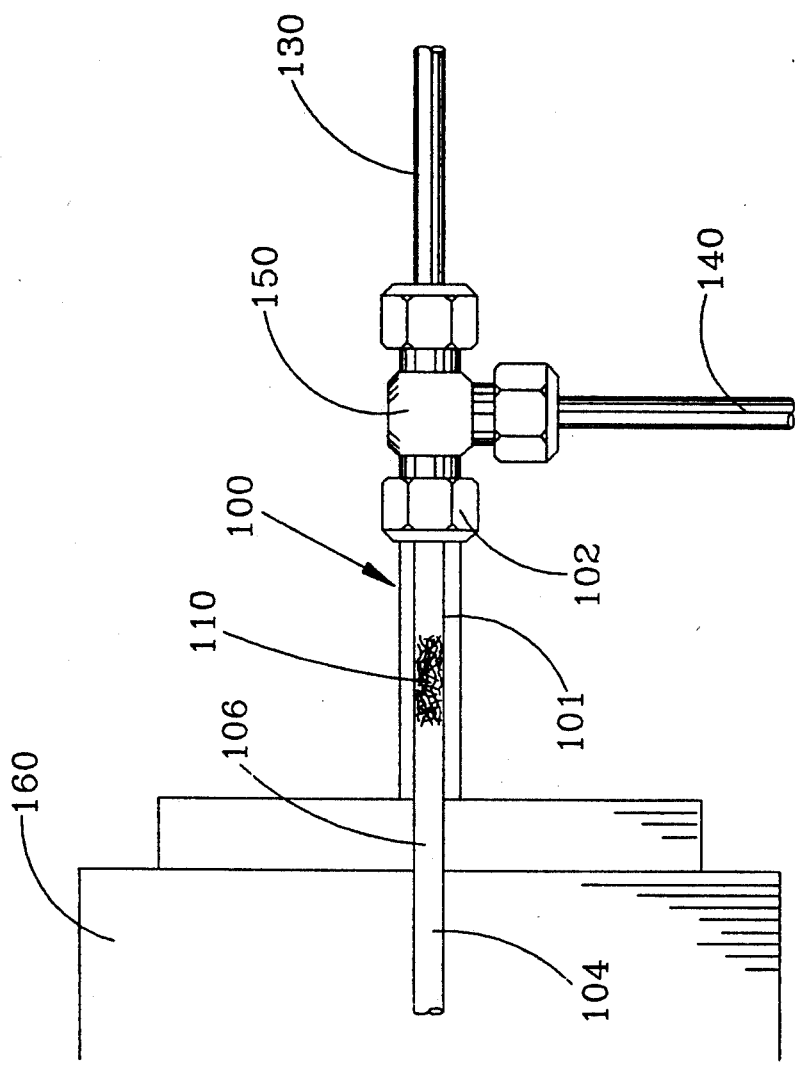
FIG. 1 is an illustration of one embodiment of a sample dispersing apparatus and method for use in combination with a pyrolysis furnace as practiced by the present invention.

The above general description and the following detailed description are merely illustrative of the generic invention, and additional modes, advantages and particulars of this invention will be readily suggested to those skilled in the art without departing from the spirit and scope of the invention.

DETAILED DESCRIPTION OF THE PREFERRED EMBODIMENTS

Reference will now be made in detail to the present preferred embodiments of the invention as described in the accompanying drawings.

FIG. 1 illustrates a dispensing apparatus 100. The dispensing apparatus 100 comprises a conduit 101 having an input aperture 102 and an exit aperture 104. The conduit 101 has, between the input aperture 102 and the exit aperture 104, a channel 106 there through. Engaged within the channel 106 of the conduit 101 is a diffuser 110. The conduit 101 is attached to a tee 150 at the input aperture 102, and is attached to a pyrolysis furnace 160 at the exit aperture 104. The tee 150 has a sample input port 130 and a carrier input port 140.

The sample enters the sample input port 130 passing through the tee 150. Concurrently, if appropriate, a carrier gas enters the carrier input port 140 passing through to the tee 150. The sample engages the diffuser 110 immediately prior to entering the pyrolysis furnace 160. The diffuser 110 provides that the sample is dispersed within the cross sectional area associated with the channel 106 of the conduit 101. Thus, the sample can pass through the channel 106 toward the exit aperture 102 within the pyrolysis furnace 160 without creating deposits on the channel 106 due to the heating of the sample by the pyrolysis furnace 160.

It has been found that glass or quartz wool proves to be an adequate diffuser 110 for use in the dispensing apparatus 100. The sample input port 130 can be adapted for accepting a needle from a syringe. Using the diffuser 110 within the channel 106 associated with the pyrolysis furnace 160 provides that the carrier gas picks up all the liquids and/or sulfur for mixing and for transferring them into the high temperature zone of the pyrolysis furnace 160.

One purpose of the wool diffuser 110 is to prevent liquid hydrocarbon from entering the pyrolysis furnace 160. The sample, e.g., liquid hydrocarbon, is vaporized and mixed with the carrier gas stream prior to entering the pyrolysis furnace 160, preferably by physically retainng the liquid in the hydrogen effluent stream via the wool diffuser 110.

What is claimed is:

1. An apparatus for dispersing a sample for use in combination with a pyrolysis furnace for measuring the concentration of a fluid in a process stream or environment comprising:
   (a) a conduit having a first end for receiving the sample and a second end through which the sample emanates from said conduit, the pyrolysis furnace is operatively associated with the second end of said conduit for heating said conduit and any sample passing through said conduit; and
   (b) a dispersing device engaged within said conduit for affecting the sample to distribute the sample throughout said conduit such that the sample is heated in said conduit by the pyrolysis furnace without coking within said conduit, wherein said dispersing device engaged within said conduit comprises quartz wool.

2. An apparatus for dispersing a sample for use in combination with a pyrolysis furnace for measuring the concentration of a fluid in a process stream or environment as defined in claim 1 further comprising means for mixing a carrier gas with the sample prior to engaging said dispersing device.

3. An apparatus for dispersing a sample for use in combination with a pyrolysis furnace for measuring the concentration of a fluid in a process stream or environment as defined in claim 2 wherein said means for mixing a carrier gas with the sample comprises a tee having a first inlet, a second inlet and an outlet for accepting the sample through said first inlet, for accepting the carrier gas through said second inlet and egressing the mixture of sample and carrier gas through the outlet.

4. An apparatus for dispersing a sample for use in combination with a pyrolysis furnace for measuring the concentration of a fluid in a process stream or environment as defined in claim 1 wherein said conduit is a cylindrical member.

5. An apparatus for dispersing a sample for use in combination with a pyrolysis furnace for measuring the concentration of a fluid in a process stream or environment as defined in claim 1 further comprising a spacing device for displacing said conduit from the pyrolysis furnace.

6. An apparatus for dispersing a sample for use in combination with a pyrolysis furnace for measuring the concentration of a fluid in a process stream or environment as defined in claim 1 wherein said spacing device comprises a cylindrical sleeve which engages therein said conduit.

7. A method for dispersing a sample for use in combination with a pyrolysis furnace for measuring the concentration of a fluid in a process stream or environment comprising the steps of:
   (a) receiving a sample into a first end of a conduit having a channel there through,
   (b) passing the sample down the channel in the conduit, (c) dispersing the sample throughout the cross section of said conduit by engaging the sample with quartz wool, (d) moving the dispersing sample down the channel in the conduit, and
(e) engaging the dispersing sample in the channel of the conduit with the pyrolysis furnace for initiating the pyrolization.

* * * * *

UNITED STATES PATENT AND TRADEMARK OFFICE
CERTIFICATE OF CORRECTION

PATENT NO. : 5,241,868
DATED : September 7, 1993
INVENTOR(S) : W. Jay Szinyei

It is certified that error appears in the above-indentified patent and that said Letters Patent is hereby corrected as shown below:

On the Title Page, Item [54], line 2, change "Pyrolisis" to --Pyrolysis--.

On the Title Page , under the designation of Attorney, Agent, or Firm, change "Samecki" to --Zamecki--.

On the Title Page, Item[57], line 23, change "pyrolization" to --pyrolyzation--.

In column 3, line 13, change "pyrolization" to --pyrolyzation--.

In column 6, line 5, change "pryolization" to --pyrolyzation--.

Signed and Sealed this

Nineteenth Day of April, 1994

*Attest:*

BRUCE LEHMAN

*Attesting Officer*  *Commissioner of Patents and Trademarks*